United States Patent [19]

Nagawa et al.

[11] Patent Number: 5,142,901
[45] Date of Patent: Sep. 1, 1992

[54] SPECIFIC HEAT BASED MOISTURE SENSOR

[75] Inventors: Yoshiharu Nagawa; Yoshiaki Ishiguro, both of Shizuoka, Japan

[73] Assignee: Yazaki Corporation, Japan

[21] Appl. No.: 589,593

[22] Filed: Sep. 28, 1990

[30] Foreign Application Priority Data

Oct. 25, 1989 [JP] Japan .......................... 1-124036[U]

[51] Int. Cl.⁵ .......................... G01N 25/56; G01K 7/10
[52] U.S. Cl. .......................... 73/73; 136/232; 374/179; 374/182
[58] Field of Search .............. 73/73, 75, 77; 136/232; 374/45, 54, 136, 141, 155, 179, 182

[56] References Cited

U.S. PATENT DOCUMENTS

| | | | |
|---|---|---|---|
| 2,718,141 | 9/1955 | Richards | 73/75 |
| 4,018,624 | 4/1977 | Rizzolo | 136/232 |
| 4,020,417 | 4/1977 | Brehob | 73/73 X |
| 4,165,633 | 8/1979 | Raisanen | 73/76 |
| 4,238,957 | 12/1980 | Bailey et al. | 136/232 X |
| 4,242,906 | 1/1981 | Briscoe et al. | 73/73 |
| 4,399,404 | 8/1983 | Resh | 73/73 X |
| 4,445,788 | 5/1984 | Twersky et al. | 73/73 X |
| 4,453,401 | 6/1984 | Sidey | 73/73 |
| 4,527,909 | 7/1985 | Dale et al. | 374/179 X |
| 4,531,087 | 7/1985 | Larson | 73/73 X |
| 4,614,442 | 9/1986 | Poney | 374/209 X |
| 4,673,306 | 6/1987 | Wilhelmson et al. | 374/182 |
| 4,721,534 | 1/1988 | Phillippi et al. | 374/179 X |
| 4,845,978 | 7/1989 | Whitford | 374/45 X |
| 4,934,831 | 6/1990 | Volbrecht | 374/163 |

FOREIGN PATENT DOCUMENTS

| | | |
|---|---|---|
| 59-72784 | 4/1984 | Japan .................................. 132/232 |
| 63-47644 | 2/1988 | Japan . |

Primary Examiner—William A. Cuchlinski, Jr.
Assistant Examiner—G. Bradley Bennett
Attorney, Agent, or Firm—Wigman & Cohen

[57] ABSTRACT

A specific heat based moisture sensor comprises: a cylindrical member formed with two parallel axially-extending hollow portions; a heater provided on an outer circumferential surface of the cylindrical member; a temperature sensor formed by leads passed through the two hollow portions of the cylindrical member; and a waterproof synthetic resin formed so as to cover said cylindrical member and the heater. Since the difference in distance between the heater and the temperature sensor lead is determined precisely, the sensing reliability can be improved. Since the ceramic cylindrical member is used, temperature sensitivity can be improved. Since the sensor is covered with a waterproof resin, it is possible to prevent metallic ions from entering the substance to be sensed, without increasing the size and cost of the moisture sensor.

2 Claims, 5 Drawing Sheets

SPECIFIC HEAT BASED MOISTURE SENSOR

BACKGROUND OF THE INVENTION

1. Field of Invention

The present invention relates to an improvement in a specific heat based moisture sensor, and more specifically to a specific heat based moisture sensor for measuring moisture content included in moisture bearing substances such as soil, sand, rock wool used for gardening facility, caltivation apparatus, etc.

2. Description of the Prior Art

In cultivation apparatus provided with a culture medium carrier such as rock wool, for instance, it is very important to measure and control the moisture content thereof, because the moisture content of the culture medium carrier exerts a serious influence upon the growth of cultured plants.

The same applicant has already proposed a specific heat based moisture sensor which can measure moisture content more easily and quickly than the conventional tension meter- or infrared ray-based moisture measurement instruments, in Japanese Published Unexamined (Kokai) Patent Appli. No. 63-47644.

In the specific heat based moisture sensor disclosed in the above Japanese patent document, a cylindrical metallic vessel is closed at one end and opened at the other end; wires are taken out of the open end thereof; a heater is provided within the vessel; a first high temperature sensor is arranged within the vessel a predetermined distance apart from the heater; a second low temperature sensor is arranged within the vessel without being subjected to the influence of heat of the heater; the vessel is filled with a plastic as a heat loss substance; and the wires are connected to a moisture meter.

In use of the above-mentioned specific heat based moisture sensor, the cylindrical vessel is inserted into the substance to be measured (e.g. culture medium carrier) and the heater is activated. In this case, although the heat is transmitted from the heater to the first high temperature sensor, since part of heat quantity of the substance to be measured is absorbed into the substance according to the moisture content of the substance, it is possible to measure the moisture content of the substance by measuring a change in temperature between the two temperature sensors, while keeping the heating power of the heater at a constant value.

In the above-mentioned proposed moisture sensor, since the cylindrical vessel is made of metal, there exists a serious problem in that the vessel is corroded and therefore metallic ions are produced and enter the culture medium, so that the cultured plant is subjected to a harmful influence of these ions.

SUMMARY OF THE INVENTION

With these problems in mind, therefore, it is the primary object of the present invention to provide a specific heat based moisture sensor which can prevent the cylindrical vessel from being corroded and therefore prevent metallic ions from entering the culture medium, and additionally can measure moisture content of the substance to be measured quickly and precisely without increasing the cost and the size thereof.

To achieve the above-mentioned object, the specific heat based moisture sensor according to the present invention comprises: (a) a cylindrical member (20) formed with two parallel axially-extending hollow portions (21, 22); (b) a heater (30) provided on an outer circumferential surface of said cylindrical member; (c) a temperature sensor (40, 41, 42) formed by leads passed through the two hollow portions of said cylindrical member; and (d) a waterproof synthetic resin (60) formed so as to cover said cylindrical member and said heater.

The cylindrical member is made of ceramic to improve the temperature sensitivity from the outer heater to the inner temperature sensor. The waterproof synthetic resin vessel is formed with a sharp tip to facilitate insertion of the sensor into substance to be measured. The temperature sensor is a thermocouple including a first wire and a second wire connected in such a way that a first high temperature sense point between the two wires is located within one of the cylindrical hollow portion of the cylindrical member and a second low temperature sense point between the two wires is located outside the cylindrical hollow portion thereof. The heater is a nichrome wire wound around the outer circumferential surface of the cylindrical member at regular pitches.

In the specific heat based moisture sensor according to the present invention, the cylindrical member is formed with two axially extending hollow portions through which wire is passed; a heater is wound around the outer circumference of the cylindrical portion; and further the cylindrical member and the heater are molded integral with each other by a waterproof synthetic resin. Therefore, it is possible to reduce the difference in the distance between the heater and the temperature sensor among manufactured products, simplify the manufacturing process, minimize the shape and the cost thereof, and further eliminating the harmful influence upon the cultured plant due to metallic corrosion.

Further, since the end of the specific heat based moisture sensor according to the present invention is formed into a sharp tip, it is possible to easily insert the sensor into the substance to be measured such as a culture medium carrier, thus facilitating the measurement process.

Further, in the moisture sensor according to the present invention, since a ceramic cylindrical member (whose thermal conductivity is higher than that of resin) is used for the cylindrical member for supporting the heater and the sensor, it is possible to improve the sensor sensitivity with respect to heat, thus permitting higher sensitivity and higher precision measurement of moisture content.

In summary, the specific heat based moisture sensor according to the present invention can improve the detection sensitivity and precision of moisture content, simplify the measurement, and reduce the shape and cost thereof, thus realizing a specific heat based moisture sensor of higher performance as compared with the conventional specific heat moisture sensor.

DETAILED DESCRIPTION OF THE PREFERRED EMBODIMENTS

An embodiment of the specific heat based moisture sensor according to the present invention will be described in further detail with reference to the attached drawings.

Figure 1:
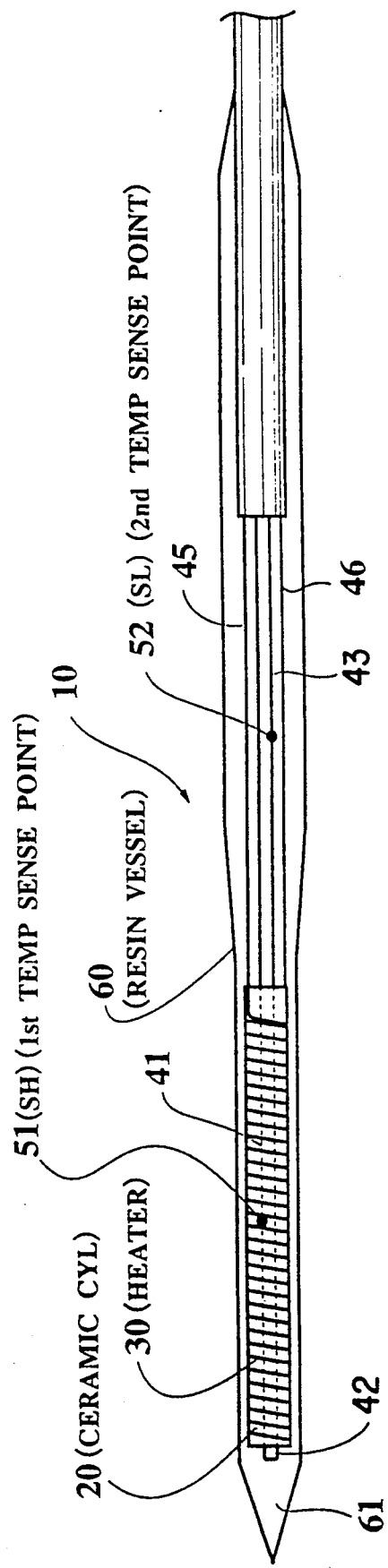
FIG. 1 is an illustration for assistance in explaining the specific heat based moisture sensor according to the present invention.
Figure 2:
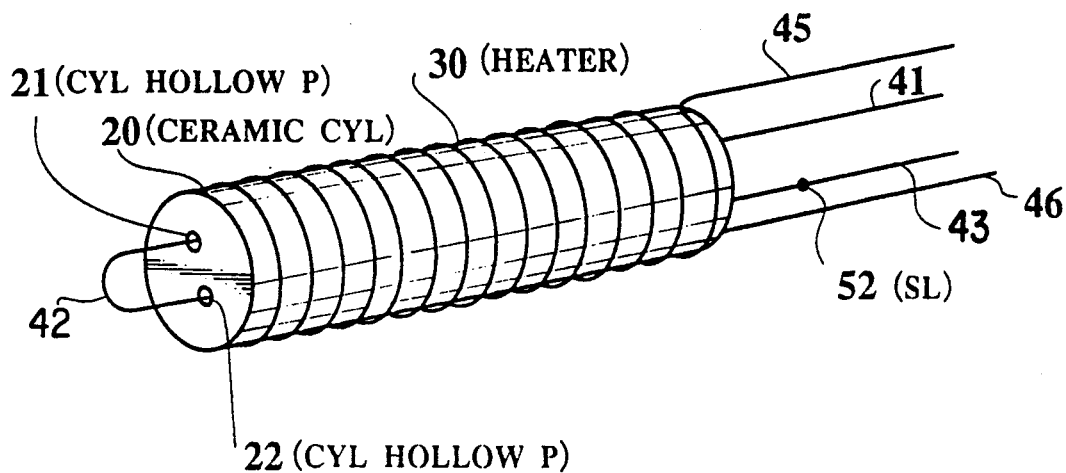
FIG. 2 is a perspective view showing the ceramic cylindrical member shown in FIG. 1.

FIG. 1 is a side view showing a specific heat based moisture sensor according to the present invention, and FIG. 2 is a perspective view showing a ceramic cylindrical member shown in FIG. 1.

In FIGS. 1 and 2, the specific heat based moisture sensor 10 according to the present invention comprises a ceramic cylindrical member 20 formed with two axially extending cylindrical hollow portions 21 and 22, a nichrome heating wire 30 wound around an outer circumferential surface of the cylindrical member 20 at regular pitch intervals, a thermocouple composed of a first lead 41, second lead 42 both passed through these two cylindrical hollow portions 21 and 22 and a third lead 43, a first high temperature sense point 51 connected between the first lead 41 and a second lead 42 within the cylindrical member 20 so as to be heated by the heater 30, a second low temperature sense point 52 connected between the second lead 42 and the third lead 43 outside the cylindrical member 20 so as not to be subjected to the influence of heat of the heater 30, and a waterproof synthetic resin tubular vessel 60. The first and third leads 41 and 43, respectively, are led out of the tubular vessel 60 and connected to a moisture meter (not shown). Further, the heater 30 is led out of the tubular vessel 60 via two heater leads 45 and 46 and connected to a power source E via a switch SW (both shown in FIG. 3).

The thermocouple is a temperature sensor in which two different metallic wires are connected in a ring shape and an electromotive force (V) generated between the free ends of the one wire is measured by a voltammeter when two junction points are placed at two different temperatures. In practice, a first junction point is kept at a constant temperature, and the temperature at a second junction point is detected on the basis of the measured electromotive force (V). The two different metals are platinum and platinum rhodium (300° to 1400° C.), alumel and chromel (0° to 750° C.), iron and constantan, etc.

Without being limited to the thermocouple, it is also possible to use a platinum thin film resistor or other temperature sensors for the moisture sensor according to the present invention.

The ceramics used for forming the cylindrical member 20 include sintered bodies of metallic oxide, boride, carbide and nitride of silane, aluminium, magnesium, zinc, etc. or these mixtures and compounds, which are excellent in strength and heat resistance.

The synthetic resin tubular vessel 60 is formed of a waterproof synthetic resin such as glass fiber reinforcing polybutyleneterephtarate, and preferably formed with a pencil-shaped sharp end (tip) portion 61 to facilitate insertion of the sensor 10 into a substance to be inspected.

Figure 3:
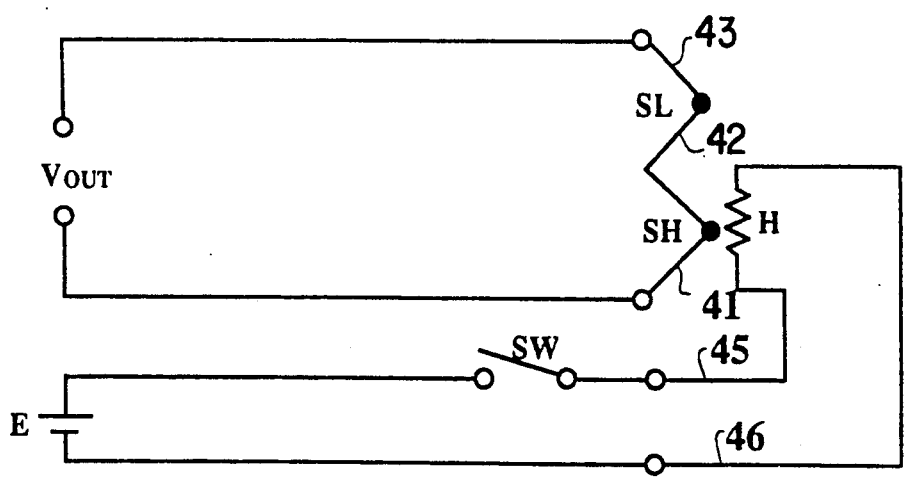
FIG. 3 is a basic circuit diagram of the specific heat based moisture sensor according to the present invention.

FIG. 3 shows a basic circuit of the thermocouple moisture sensor according to the present invention, in which E denotes a power source such as a battery; H (30) denotes a nichrome heating wire; $V_{out}$ denotes a sensor output voltage; SH (51) denotes a high temperature sense point; and SL (52) denotes a low temperature sense point.

When the moisture content of a substance to be checked is required to be measured by use of the moisture sensor according to the present invention, the sharp end portion 61 of the sensor 10 is inserted into the substance and a constant voltage is supplied from the battery E to the heater H (30) to generate heat from the heater H (30). In this case, where the substance includes moisture, since part of heat from the heater H (30) is absorbed into the substance according to the degree of the moisture content, a change in temperature at the high temperature sense point SH (51) is measured to detect the moisture content, on condition that the heat quantity generated by the heater H (30) is kept constant, in comparison with the temperature at the low temperature sense position SL (52).

In the moisture sensor according to the present invention, since the cylindrical member 20 is formed of ceramics, the thermoconductivity is high and therefore the heat loss is small, thus improving the sensor sensitivity.

Further, since the measurement time can be reduced as short as about 60 sec, it is possible to economize the battery power, thus allowing the moisture sensor to be most suitable for use together with a portable moisture meter.

In addition, since the moisture sensor according to the present invention is molded integral in the form of a synthetic resin tubular vessel 60, the manufacturing process can be simplified and the manufacturing cost can be reduced. Further, since the end 61 of the synthetic resin tubular vessel 60 is formed into a sharp shape, the sensor 10 can be easily inserted into a substance to be checked. Further, since the sensor 10 is covered by a synthetic resin entirely, it is possible to eliminate the harmful influence upon the cultured plant due to corrosion or rust or metallic ion generation from the corroded metal. Furthermore, since the distance between the thermocouple temperature sensor element 40 within the two hollow portions and the heater 30 wound outside the cylindrical member 20 can be kept constant at any time, it is possible to reduce the difference in performance between the manufactured sensors.

The effect of the specific heat moisture sensor according to the present invention will be explained on the basis of test examples.

TEST EXAMPLE 1

Rock wool measurement

A well dried rock wool was cut into a 30×30×7.5 cm size, and the weight and volume was measured. The sharp end of the moisture sensor according to the present invention was inserted into a middle position of a height (7.5 cm) of the 30×30 cm rock wool for measurement preparation.

Thereafter, water is supplied from under the rock wool for about 30 min to allow the rock wool to contain water all over it. The water content rate of the entire rock wool was measured as 90 volume %. Under these conditions, a voltage of 6.0 V was applied to the nichrome heating wire for about 1 min to measure the thermocouple electromotive force. Further, the water content rate of the rock wool was adjusted to 70, 50 and 30 volume %, and the thermocouple electromotive forces were measured under the same conditions. These measured results are plotted by white circles in FIG. 4.

On the other hand, a prior-art moisture sensor in which a Teflon (Trademark) cylindrical member was insertion molded within the synthetic resin vessel instead of the ceramic cylindrical member was prepared, and the thermocouple electromotive forces were measured under the same conditions for comparison. These measured results are plotted by black circles in FIG. 4.

Further, the electromotive forces of the prior-art moisture sensor provided with the Teflon cylindrical member were measured on condition that the measurement time was 3 min. These measured results are plotted by black triangles in FIG. 4.

Figure 4:
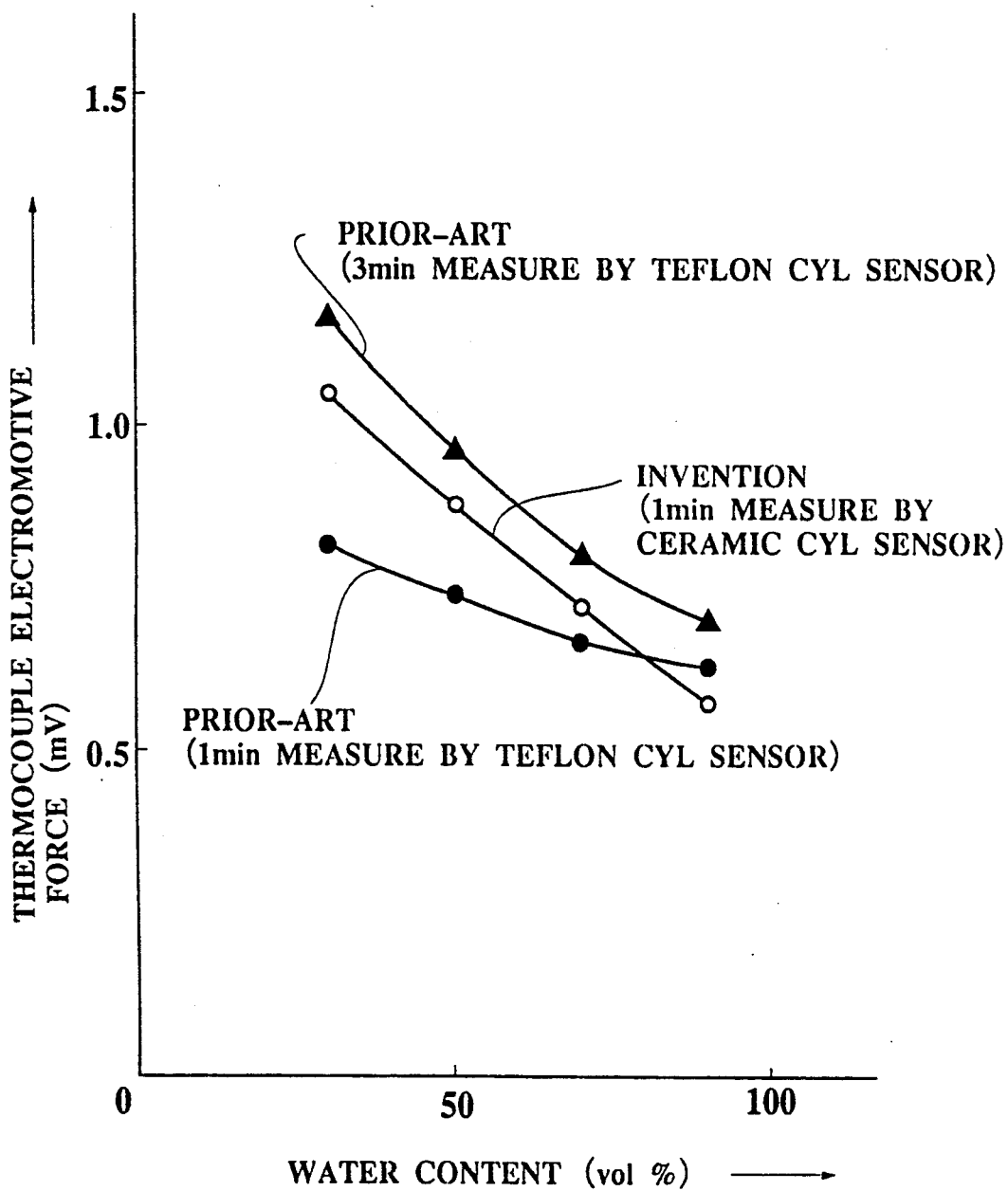
FIG. 4 is a graphical representation showing the relationship between the volumetric moisture content rate (abscissa) and the sensor electromotive force (ordinate) obtained when moisture content in a rock wool was measured by the moisture sensor according to the present invention in comparison with the prior-art moisture sensor.

FIG. 4 indicates that a difference in the electromotive force of the invention moisture sensor at the measurement time of 1 min is roughly equal to that of the prior-art moisture sensor at the measurement time of 3 min. However, since FIG. 4 indicates that the gradient of electromotive force in the invention moisture sensor is larger than that in the prior-art moisture sensor in the higher water content range (at about 90 volume %), the invention moisture sensor is high in measurement sensitivity all over the water content range and in the higher water content range, in particular. Further, the difference in the electromotive force between 30 and 90 volume % of the invention sensor is twice larger than that of the prior-art sensor. This indicates the higher sensitivity all over the water content range.

TEST EXAMPLE 1

Black soil measurement

Water was added little by little to well dried black soil and mixed therewith to obtain samples of 10, 20, 30 and 36% by weight in water content rate. Each of these samples was put into a plastic container. The moisture sensor according to the present invention was inserted vertically into each of these samples at four different positions. A voltage of 6 V was applied to the nichrome wire for 60 sec for each measurement to measure the thermocouple electromotive force. The measured results are plotted by white circles in FIG. 5.

Figure 5:
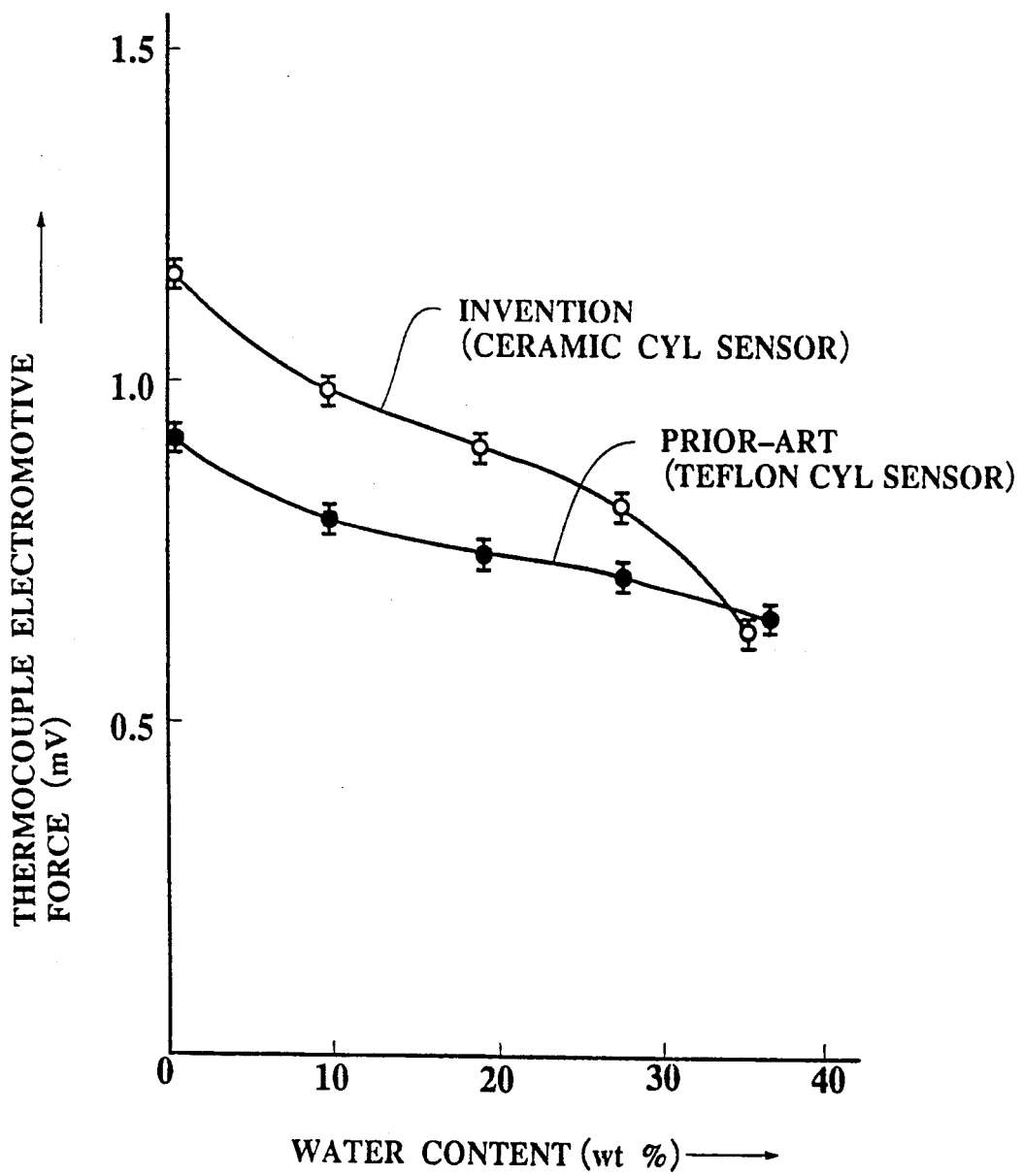
FIG. 5 is a graphical representation showing the relationship between the weight moisture content rate (abscissa) and the sensor electromotive force (ordinate) obtained when moisture content in a black soil was measured by the moisture sensor according to the present invention in comparison with the prior-art moisture sensor.

FIG. 5 indicates that the maximum measurement dispersion at each different measurement point is about ±2 to 3% (shown by a short vertical line) and it is possible to practically use the moisture sensor according to the present invention even in such a short measurement time as 60 sec. Further, the gradient of the thermocouple electromotive force is sharp in a higher water content range and therefore the sensor sensitivity is high in the high water content range.

On the other hand, a prior-art moisture sensor in which a Teflon cylindrical member was insertion molded within the synthetic resin vessel instead of the ceramic cylindrical member was prepared, and the thermocouple electromotive forces were measured under the same conditions for comparison. These measured results are plotted by black circles in FIG. 5.

FIG. 5 indicates that the maximum measurement dispersion at each different measurement point is almost the same as that (2 to 3%) of the present invention. However, since the difference in measurement value between 10 and 36 weight % of the prior-art sensor is small, the measurement error increases as high as 8 to 10% at the maximum all over the water content range, and therefore the measurement time of 60 sec is not sufficient for the prior-art sensor. This is because the sensor sensitivity of the prior-art sensor is not sufficient as compared with that of the invention sensor.

Figure 6:
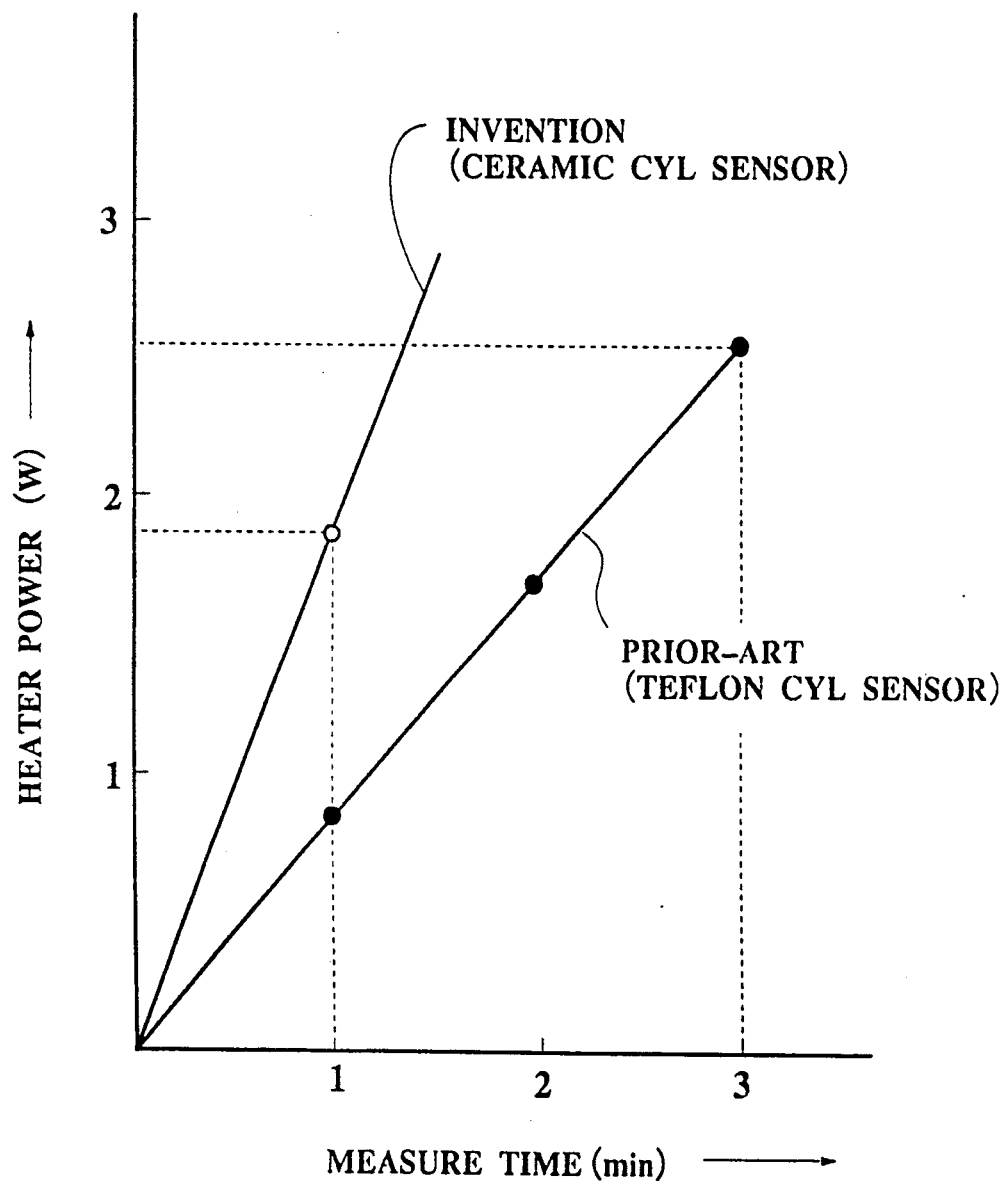
FIG. 6 is a graphical representation showing the relationship between the measurement time (abscissa) and the heater power (ordinate) consumed when moisture content was measured.

Further, FIG. 6 shows the relationship between the consumed heater power (W) and the measurement time in each of the invention moisture sensor and the prior-art moisture sensor, when moisture content was measured.

FIG. 6 indicates that the invention moisture sensor consumes about 1.9 W in each sufficient measurement time of 1 min but the prior-art moisture sensor consumes about 2.55 W in each sufficient measurement time of 3 min, thus economizing the power consumption rate as much as about 30% in the case of the moisture sensor according to the present invention.

As described above, in the specific heat based moisture sensor according to the present invention, it is possible to improve the detection sensitivity and precision, reduce the size and the cost, simplify the measurement process, etc. thus realizing a specific heat based moisture sensor of higher performance as compared with the prior-art specific heat based moisture sensor.

What is claimed is:

1. A specific heat based moisture sensor, comprising:
   (a) a cylindrical member formed as a separate unit with two parallel axially-extending hollow portions formed therein to accomodate wires of a temperature sensor passed therethrough;
   (b) a heater provided on an outer circumferential surface of said cylindrical member;
   (c) a temperature sensor of thermocouple type formed by leads passed through the two hollow portions of said cylindrical member, said temperature sensor having:
      (1) a first wire;
      (2) a second wire;
      (3) a third wire; and
      (4) a first high temperature sense point between said first and second wires being located within one of the cylindrical hollow portions of said cylindrical member and a second low temperature sense point between said second and third wires being located outside said cylindrical hollow portions of said cylindrical member; and
   (d) a waterproof synthetic resin formed so as to cover said cylindrical member and said heater, whereby moisture content of a substance is detected by measuring a change in temperature between the two temperature sense points, when said cylindrical member is inserted into the substance to be measured, while keeping heating power at a constant value.

2. The specific heat based moisture sensor of claim 1, wherein said cylindrical member is made of ceramic.

* * * * *